US00PP25833P2

(12) United States Plant Patent
Stephens

(10) Patent No.: US PP25,833 P2
(45) Date of Patent: Aug. 25, 2015

(54) ***DISTYLIUM* PLANT NAMED 'SPG-3-007'**

(50) Latin Name: *Distylium myricoides*
Varietal Denomination: sPg-3-007

(71) Applicant: Carroll T. Stephens, North Augusta, SC (US)

(72) Inventor: Carroll T. Stephens, North Augusta, SC (US)

(73) Assignee: Southern Plant Group, Atlanta, GA (US)

( * ) Notice: Subject to any disclaimer, the term of this patent is extended or adjusted under 35 U.S.C. 154(b) by 152 days.

(21) Appl. No.: 13/987,779

(22) Filed: Aug. 31, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Distylium* plant named 'sPg-3-007', characterized by its compact and outwardly spreading plant habit; freely branching habit, dense and bushy plant form; dark purple-colored stems leaves; light yellow-colored developing leaves occasionally with dark green-colored speckles; relatively small fully developed leaves that are dark green in color; and good container and garden performance.

3 Drawing Sheets

Botanical designation: *Distylium myricoides*.
Cultivar denomination: 'sPg-3-007'.

BACKGROUND OF THE INVENTION

The present invention relates to a new and distinct *Distylium* plant, botanically known as *Distylium myricoides* and hereinafter referred to by the name 'sPg-3-007'.

The new *Distylium* plant is a naturally-occurring branch mutation of an unnamed proprietary selection of *Distylium myricoides,* not patented. The new *Distylium* plant was discovered and selected by the Inventor on a single plant from within a population of plants of the unnamed proprietary selection in a controlled nursery environment in North Augusta, S.C. in June, 2006.

Asexual reproduction of the new *Distylium* plant by semi-hardwood cuttings in a controlled environment in North August, S.C. since June, 2006 has shown that the unique features of this new *Distylium* plant are stable and reproduced true to type in successive generations.

SUMMARY OF THE INVENTION

Plants of the new *Distylium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'sPg-3-007'. These characteristics in combination distinguish 'sPg-3-007' as a new and distinct *Distylium* plant:

1. Compact and outwardly spreading plant habit.
2. Freely branching habit, dense and bushy plant form.
3. Dark purple-colored stems leaves.
4. Developing leaves that are light yellow in color occasionally with dark green-colored speckles.
5. Fully developed leaves that are dark green in color and relatively small.

6. Good container and garden performance.

Plants of the new *Distylium* can be compared to plants of the parent selection. Plants of the new *Distylium* differ primarily from plants of the parent selection in the following characteristics:

1. Plants of the new *Distylium* are more compact than and not as vigorous as plants of the parent selection.
2. Plants of the *Distylium* and the parent selection differ in stem color as plants of the parent selection have olive green-colored stems.
3. Plants of the *Distylium* and the parent selection differ in developing leaf color as plants of the parent selection have olive green-colored developing leaves.

Plants of the new *Distylium* can also be compared to plants of *Distylium myricoides* 'Vintage Jade', not patented. In side-by-side comparisons, plants of the new *Distylium* differed primarily from plants of 'Vintage Jade' in the following characteristics:

1. Plants of the new *Distylium* were more compact than plants of 'Vintage Jade'.
2. Plants of the *Distylium* and 'Vintage Jade' differed in developing stem color as plants of 'Vintage Jade' had light green-colored stems.
3. Plants of the new *Distylium* had smaller leaves than plants of 'Vintage Jade'.
4. Plants of the *Distylium* and 'Vintage Jade' differed in developing leaf color as plants of 'Vintage Jade' had light green-colored developing leaves.

BRIEF DESCRIPTION OF THE PHOTOGRAPHS

The accompanying colored photographs illustrate the overall appearance of the new *Distylium* plant showing the colors as true as it is reasonably possible to obtain in colored reproductions of this type. Colors in the photographs may differ slightly from the color values cited in the detailed botanical description which accurately describe the colors of the new *Distylium* plant.

The photograph on the first sheet is a side perspective view of a typical plant of 'sPg-3-007'.

The photograph on the second sheet is a close-up view of a typical plant of 'sPg-3-007'.

The photograph on the third sheet is a close-up view of a typical flowering plant of 'sPg-3-007'.

DETAILED BOTANICAL DESCRIPTION

The aforementioned photographs and following observations, measurements and values describe plants grown during the spring and summer in seven-gallon containers in an outdoor nursery in Park Hill, Okla. and under cultural practices typical of commercial *Distylium* production. During the production of the plants, day temperatures averaged 22° C. and night temperatures averaged 9° C. Plants were three years old when the photographs and the description were taken. In the description, color references are made to The Royal Horticultural Society Colour Chart, 1995 Edition, except where general terms of ordinary dictionary significance are used.

Botanical classification: *Distylium myricoides* 'SPg-3-007'.

Parentage: Naturally-occurring branch mutation of an unnamed proprietary selection of *Distylium myricoides*, not patented.

Propagation:

*Type.*—By semi-hardwood cuttings.

*Time to initiate roots, summer.*—About six weeks at soil temperatures ranging from 24° C. to 29.5° C.

*Time to initiate roots, winter.*—About nine weeks at soil temperatures ranging from 15.5° C. to 18° C.

*Time to produce a rooted young plant, summer.*—About five to six months at soil temperatures ranging from 24° C. to 29.5° C.

*Time to produce a rooted young plant, winter.*—About seven months at soil temperatures ranging from 4.5° C. to 18° C.

*Root description.*—Medium to thin in thickness, fibrous; brown in color.

*Rooting habit.*—Freely branching; dense.

Plant description:

*Plant and growth habit.*—Perennial shrub; compact and outwardly spreading plant habit; moderately vigorous growth habit.

*Branching habit.*—Freely branching habit with lateral branches potentially developing at every node; dense and bushy plant form.

*Plant height.*—About 45.7 cm.

*Plant diameter* (*area of spread*).—About 106 cm.

Lateral branch description:

*Length.*—About 55.9 cm.

*Diameter, immature.*—About 2 mm.

*Diameter, mature.*—About 1.9 cm.

*Internode length.*—About 1.1 cm.

*Aspect.*—About 60° from vertical.

*Strength.*—Strong; flexible when immature.

*Texture.*—Pubescent, fine.

*Color, immature.*—Close to 187B becoming closer to 146B with development.

*Color, mature.*—Close to 199A.

Leaf description:

*Arrangement.*—Alternate, single.

*Length.*—About 3.4 cm.

*Width.*—About 1.1 cm.

*Shape.*—Elliptical.

*Apex.*—Acute.

*Base.*—Cuneate.

*Margin.*—Entire.

*Texture, upper surface.*—Smooth, glabrous; thick; leathery.

*Texture, lower surface.*—Pubescent, fine; thick; leathery.

*Venation pattern.*—Pinnate.

*Color.*—Developing leaves, upper surface: Close to 160B occasionally with sparse speckles, close to 1487A. Developing leaves, lower surface: Close to 160D tinged with close to 146C. Fully expanded leaves, upper surface: Close to 147A or 139A; venation, close to 147B. Fully expanded leaves, lower surface: Close to 146C and 147B; venation, close to 147C.

*Petioles.*—Length: About 2.8 mm. Diameter: About 1 mm. Texture, upper surface: Smooth, glabrous. Texture, lower surface: Pubescent, fine. Color, upper surface: Close to 146B. Color, lower surface: Close to 146C.

Flower description:

*Flower arrangement and flowering habit.*—Single flowers arranged in terminal and axillary racemes; freely flowering habit; flowers face mostly upright.

*Natural flowering season.*—Early flowering habit, plants of the new *Distylium* flower during the late winter in Oklahoma.

*Flower longevity.*—Flowers last about one week on the plant; flowers not persistent.

*Fragrance.*—None detected.

*Flower diameter.*—About 9 mm.

*Flower length.*—About 1 cm.

*Flower depth.*—About 8 mm.

*Flower buds.*—Length: About 2.6 mm. Diameter: About 1.8 mm. Shape: Ovoid. Color: Close to 199A.

*Petals.*—Flowers of the new *Distylium* are apetalous.

*Sepals.*—Arrangement: Typically four sepals in a single whorl; polysepalous. Length: About 3.2 mm. Width: About 1.5 mm. Shape: Elliptic. Apex: Acute. Base: Truncate. Margin: Entire. Texture, upper surface: Smooth, fleshy. Texture, lower surface: Lepidote; leathery. Color, upper surface: Close to 158D. Color, lower surface: Close to 147C; scales, close to 199C.

*Bracts.*—Arrangement: Typically four bracts in a single loose whorl. Length: About 3.1 mm. Width: About 0.8 mm. Shape: Globular. Apex: Acute. Base: Rounded. Margin: Entire. Texture, upper and lower surfaces: Smooth. Color, upper surface: Close to 72B. Color, lower surface: Close to 72D.

*Peduncles.*—Length: About 1.2 cm. Diameter: About 5 mm. Strength: Flexible. Texture: Pubescent, fine. Color: Close to 146C; pubescence, close to 166A.

*Pedicels.*—Length: About 2 mm. Diameter: Less than 1 mm. Strength: Flexible. Texture: Pubescent, fine. Color: Close to 146C; pubescence, close to 166A.

*Reproductive organs.*—Androecium: Stamen number: About seven to ten per flower. Filament length: About 3 mm. Filament color: Close to 146D. Anther length: About 1.8 mm. Anther color: Close to 187B. Amount of pollen: Moderate. Pollen color: Close to 158D. Gynoecium: Pistil number: Two per flower. Pistil length: About 1.1 cm. Style length: About 3 mm. Style color: Close to 146B. Stigma color: Close to 187C. Ovary color: Close to 146D.

*Fruits.*—Length: About 1 cm. Diameter: About 5 mm. Color: Close to 200C.

*Seeds.*—Length: About 5 mm. Diameter: About 2 mm. Color: Close to N200A.

Garden performance: Plants of the new *Distylium* have been observed to have good garden performance and to tolerate wind, rain and temperatures ranging from about −12° C. to about 40.5° C.

Pathogen & pest resistance: Plants of the new *Distylium* have not been observed to be resistant to pathogens and pests common to *Distylium* plants.

It is claimed:

1. A new and distinct *Distylium* plant named 'sPg-3-007' as illustrated and described.

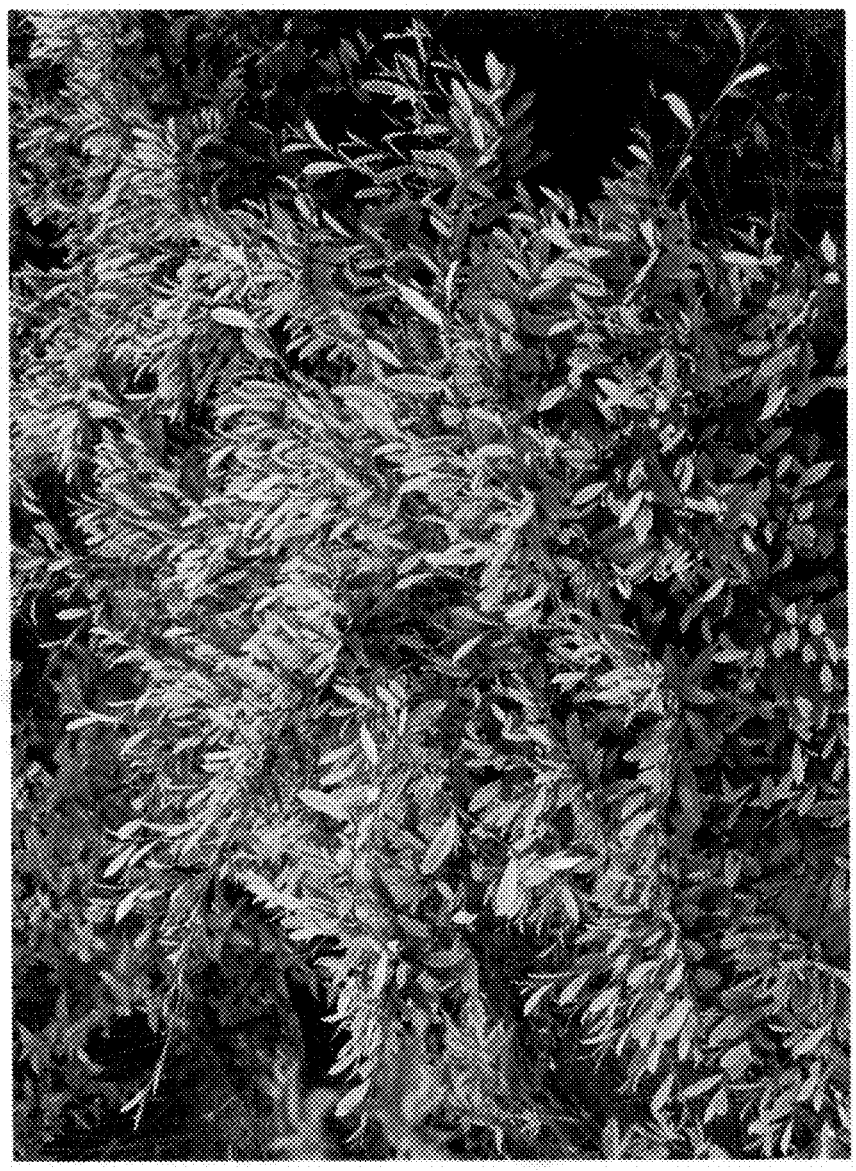

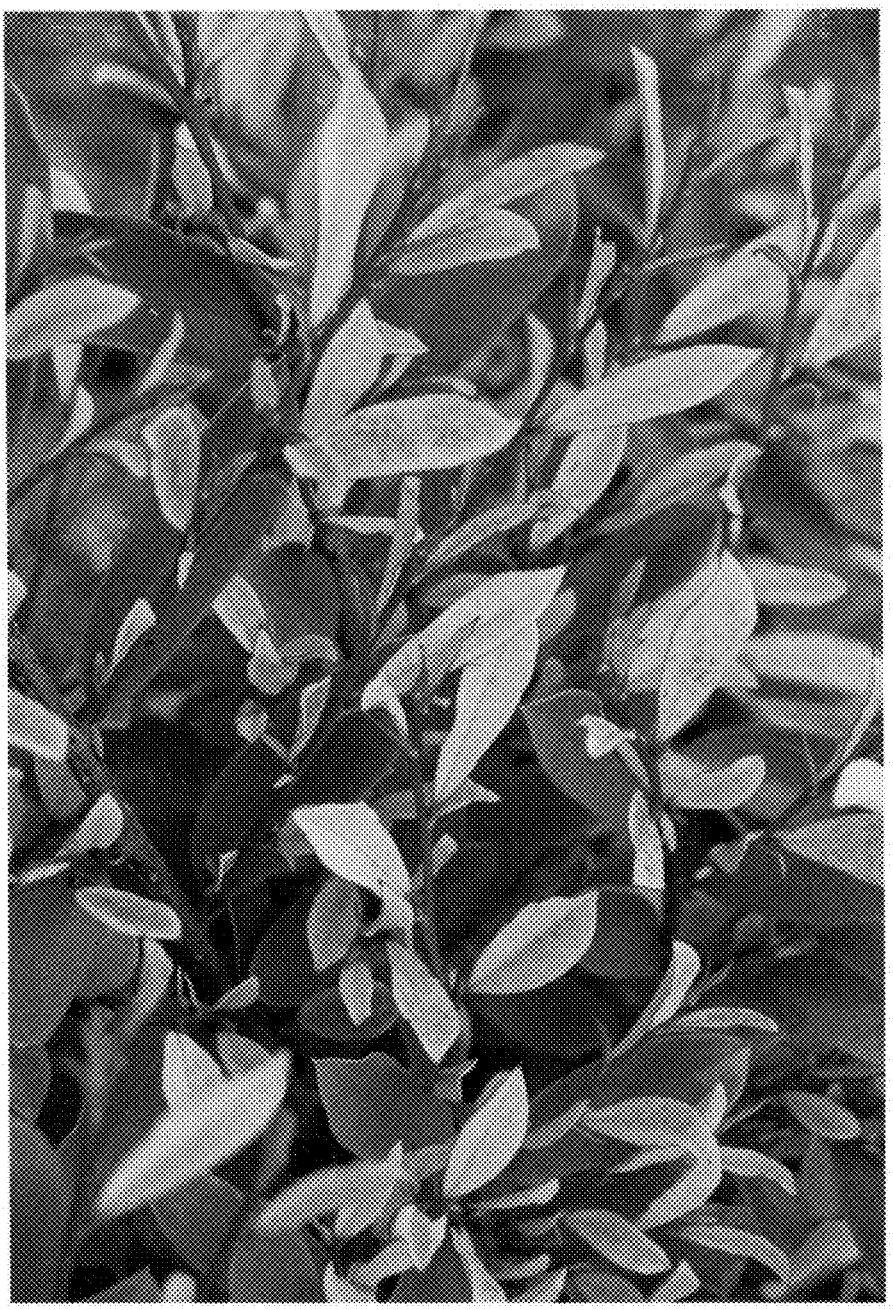

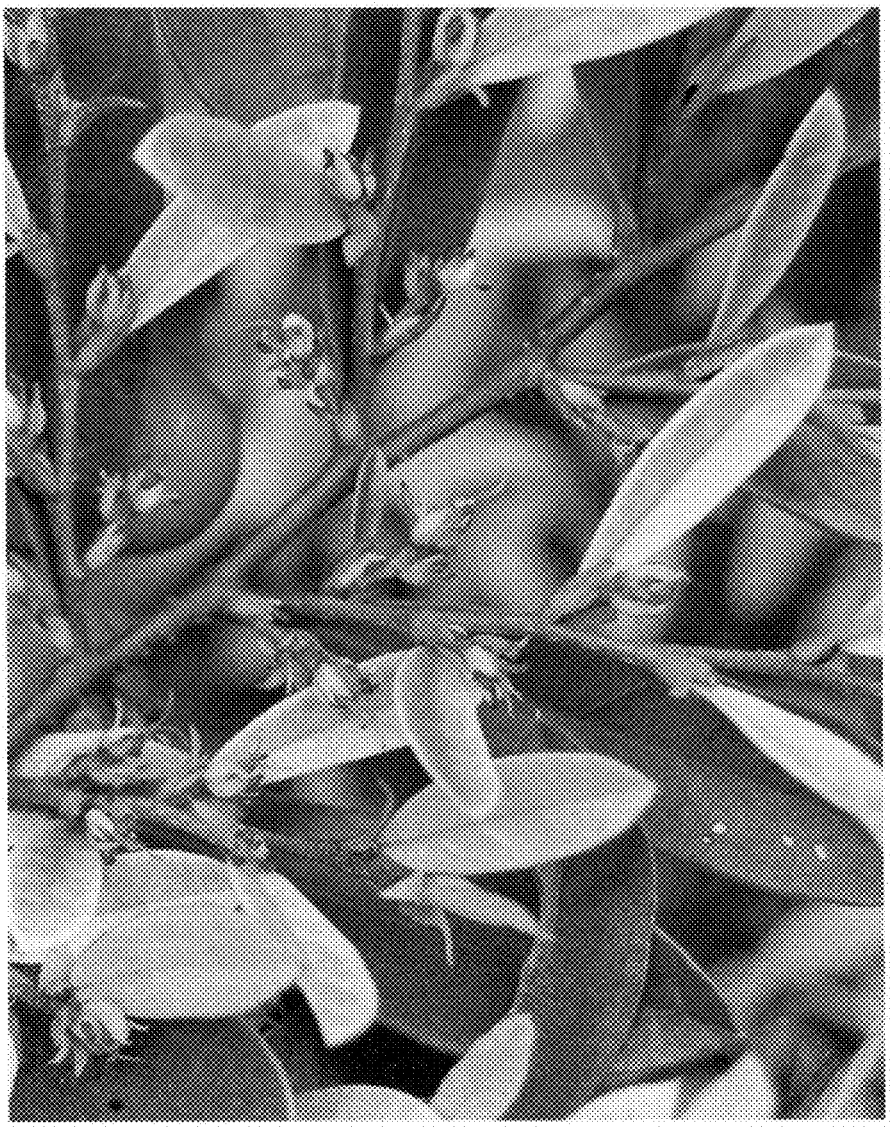

* * * * *